United States Patent
Hein et al.

(10) Patent No.: US 11,547,378 B2
(45) Date of Patent: Jan. 10, 2023

(54) APPARATUS AND METHOD COMBINING DEEP LEARNING (DL) WITH AN X-RAY COMPUTED TOMOGRAPHY (CT) SCANNER HAVING A MULTI-RESOLUTION DETECTOR

(71) Applicant: Canon Medical Systems Corporation, Otawara (JP)

(72) Inventors: Ilmar Hein, Vernon Hills, IL (US); Zhou Yu, Vernon Hills, IL (US); Tzu-Cheng Lee, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 790 days.

(21) Appl. No.: 16/509,369

(22) Filed: Jul. 11, 2019

(65) Prior Publication Data
US 2021/0007694 A1 Jan. 14, 2021

(51) Int. Cl.
*A61B 6/00* (2006.01)
*A61B 6/03* (2006.01)
(Continued)

(52) U.S. Cl.
CPC .......... *A61B 6/5205* (2013.01); *A61B 6/032* (2013.01); *A61B 6/4435* (2013.01); *G06N 3/084* (2013.01);
(Continued)

(58) Field of Classification Search
CPC ..... A61B 6/4208; A61B 6/5258; A61B 6/032; A61B 6/4266; A61B 6/4233;
(Continued)

(56) References Cited

U.S. PATENT DOCUMENTS 6,385,278 B1 5/2002 Hsieh
6,700,948 B2 3/2004 Hoffman
(Continued)

OTHER PUBLICATIONS

Changhui Jiang, et al., "Super-resolution CT Image Reconstruction Based on Dictionary Learning and Sparse Representation," Scientific Reports, Jun. 2018.
(Continued)

*Primary Examiner* — Irakli Kiknadze
(74) *Attorney, Agent, or Firm* — Oblon, McClelland, Maier & Neustadt, L.L.P.

(57) ABSTRACT

A method and apparatus is provided that uses a deep learning (DL) network together with a multi-resolution detector to perform X-ray projection imaging to provide improved resolution similar to a single-resolution detector but at lower cost and less demand on the communication bandwidth between the rotating and stationary parts of an X-ray gantry. The DL network is trained using a training dataset that includes input data and target data. The input data includes projection data acquired using a multi-resolution detector, and the target data includes projection data acquired using a single-resolution, high-resolution detector. Thus, the DL network is trained to improve the resolution of projection data acquired using a multi-resolution detector. Further, the DL network is can be trained to additional correct other aspects of the projection data (e.g., noise and artifacts).

20 Claims, 10 Drawing Sheets

(51) Int. Cl.
  *G06T 11/00* (2006.01)
  *G06N 20/00* (2019.01)
  *G06N 3/08* (2006.01)
(52) U.S. Cl.
  CPC .......... *G06N 20/00* (2019.01); *G06T 11/006* (2013.01); *G06T 2211/421* (2013.01)
(58) Field of Classification Search
  CPC ... A61B 6/5205; A61B 6/4435; A61B 5/4509; A61B 5/4842; A61B 5/7267; A61B 5/7275; A61B 6/4241; A61B 6/5282; A61B 6/037; A61B 6/482; G06T 11/006; G06T 11/005; G06T 2211/421; G06T 2211/432; G06T 7/0012; G06T 11/008; G06T 2207/20081; G06T 2207/10104; G06T 2207/20084; G06T 2207/10088; G06T 5/002; G06T 5/50; G06T 2207/30061; G06T 2207/30008; G06T 2207/10108; G06T 2207/30096; G06T 2207/10081; G06T 5/20; G06T 7/0014; G06T 2207/10072; G06T 2207/10116; G06T 2207/30004; G06T 2207/20004; G06T 7/11; G06T 2211/408; G06T 2211/40; G06T 2207/20076; G06N 3/0454; G06N 20/00; G06N 3/084; G06N 3/0481; H04N 5/32; G06V 10/82; G06V 10/454; G06V 10/30; G06V 2201/03; G06V 30/194; G06K 9/6256; G06K 9/6274; G06K 9/6231; G06K 9/0051; G06K 9/6257; G06K 9/6262; G06K 9/628; G06K 9/6282; G06K 9/6269; G01T 1/161; G01T 1/17

USPC .................... 600/407; 378/19, 62, 98.8
  See application file for complete search history.

(56) References Cited

U.S. PATENT DOCUMENTS

| | | | |
|---|---|---|---|
| 7,515,678 | B2 | 4/2009 | Hsieh et al. |
| 7,974,377 | B2 | 7/2011 | Hoffman et al. |
| 2007/0181813 | A1 | 8/2007 | DiBianca et al. |
| 2009/0080601 | A1* | 3/2009 | Tkaczyk ................ G01T 1/249 378/19 |
| 2009/0148023 | A1 | 6/2009 | Spahn |
| 2010/0215142 | A1 | 8/2010 | Dafni et al. |
| 2014/0140469 | A1 | 5/2014 | Carmi |
| 2019/0205606 | A1* | 7/2019 | Zhou ................... G06N 3/0445 |
| 2019/0244348 | A1* | 8/2019 | Buckler ................ G06N 20/00 |
| 2019/0251713 | A1* | 8/2019 | Chen ................... G06N 3/0454 |
| 2019/0325621 | A1* | 10/2019 | Wang ..................... G06N 3/084 |
| 2021/0375010 | A1* | 12/2021 | Soons ................... G06T 11/008 |

OTHER PUBLICATIONS

Prokop, M., "MDCT: Technical Principles and Future Trends," Chapter 1 in the book *Multidetector-Row Computed Tomography*, Springer-Verlag Publishers, 2005.

Cody, Dianna D. and Mahesh, Mahadevappa, "Technologic Advances in Multi-detector CT with a Focus on Cardiac Imaging," Radiographics 27:2007.

Hao Dang, et al., "Multi-resolution statistical image roconstruction for mitgation of truncation effects: application to cone beam CT of the head," Phys Med Biol. Jan. 21, 2017; 62(2): pp. 539-559.

* cited by examiner

US 11,547,378 B2

APPARATUS AND METHOD COMBINING DEEP LEARNING (DL) WITH AN X-RAY COMPUTED TOMOGRAPHY (CT) SCANNER HAVING A MULTI-RESOLUTION DETECTOR

FIELD

This disclosure relates to decreasing cost of a computed tomography scanner by using a multi-resolution detector, and, more particularly, using a deep learning (DL) neural network to preserve resolution, even though the multi-resolution detector has lower resolution in some regions than would a single-resolution detector.

BACKGROUND

Radiography systems and methods are widely used, particularly for medical imaging and diagnosis. Radiography systems generally create two-dimensional projection images through a subject's body. A radiation source, such as an X-ray tube, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector on the opposite side of the body receives radiation transmitted through the body substantially in the projection volume. The attenuation of the radiation that has passed through the body is measured by processing electrical signals received from the detector.

X-ray projection images having high spatial resolution are desirable in order to visualize fine details in the image. Further, the resolution of the reconstructed image depends on the resolution of the projection data. For example, spatial resolution can be limited by the detector pixel size. The resolution can be improved by decreasing the pixel size to have more pixels covering the same area. Decreasing the pixel size can, however, increase the cost of the detectors array, and the increased amount of data produced by more, smaller detector pixels can increase the demand for communication bandwidth to transmit the additional data from the detector across a slip ring to computer hardware performing computed tomography (CT) image reconstruction.

Accordingly, improved CT systems are desired in order to more effectively strike a balance between the tradeoff between increasing cost of the X-ray detector and the amount of data to be communicated across a slip ring on the one hand and improving resolution on the other hand.

The "background" description provided herein is for the purpose of generally presenting the context of the disclosure. Work of the presently named inventors, to the extent it is described in this background section, as well as aspects of the description which may not otherwise qualify as conventional art at the time of filing, are neither expressly nor implicitly admitted as conventional art against the present disclosure.

BRIEF DESCRIPTION OF THE DRAWINGS

A more complete understanding of the disclosure is provided by reference to the following detailed description when considered in connection with the accompanying drawings, wherein.

DETAILED DESCRIPTION

Figure 1:
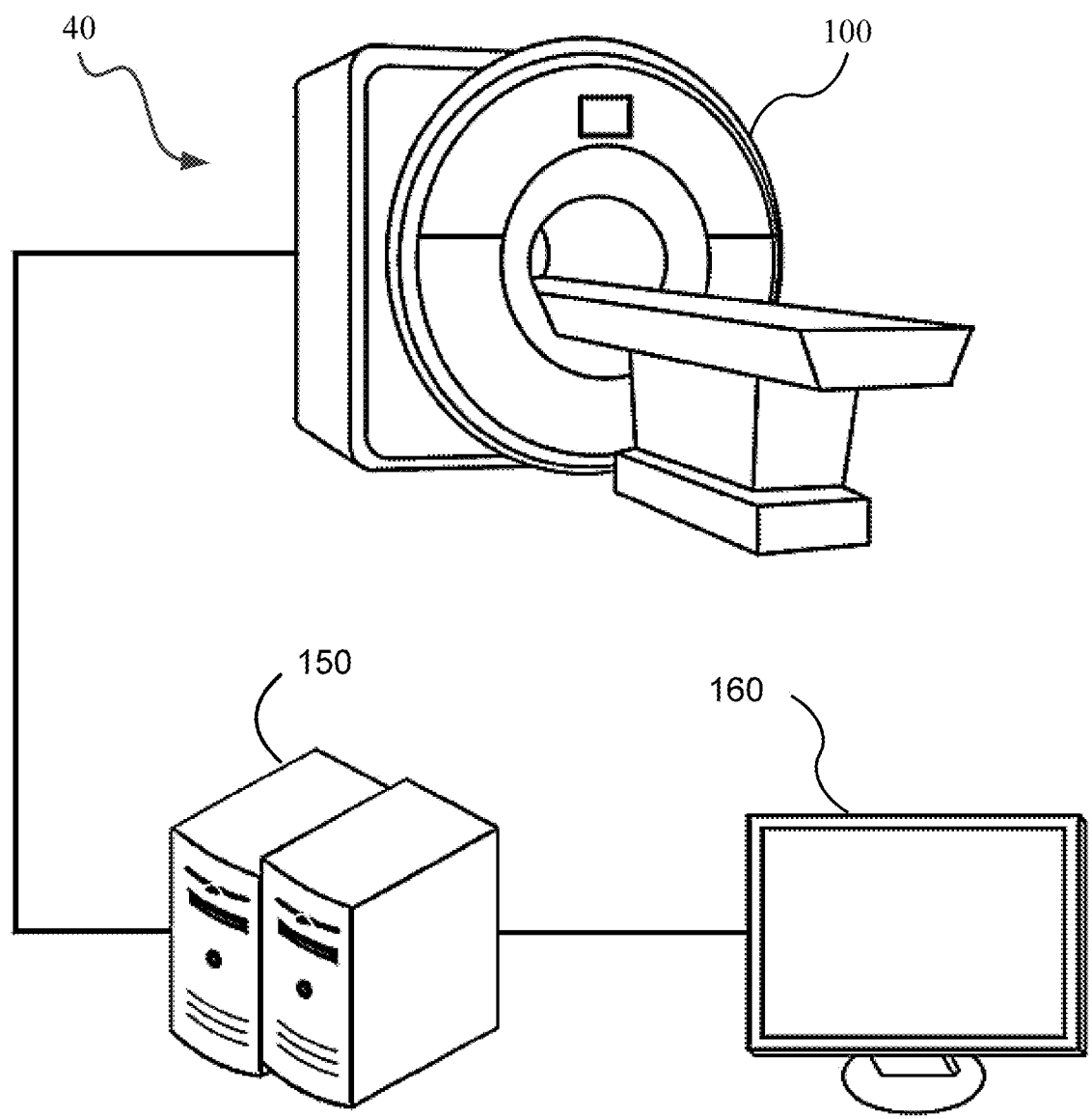
FIG. 1 shows a schematic diagram of an X-ray computed tomography (CT) system, according to one implementation.

As discussed above, there is a tradeoff between resolution on the one hand and hardware costs (e.g., the X-ray detectors and communication interface across the slip ring) on the other hand. For example, a detector array having a finer resolution (e.g., a smaller pixel pitch) and consequently more detectors in the same area costs more to fabricate than a detector array having a coarser resolution. Additionally, communication hardware having a greater bandwidth would also be required to accommodate the increase in the amount of data being generated by more detector elements.

Multi-resolution detectors can bridge this trade-off between resolution and cost. For example, higher-resolution might be beneficial mostly near the center of the field of view (FOV), allowing the detector to use a coarser resolution near the periphery of the FOV, while maintaining a finer resolution near the center of the FOV. Further, a deep learning (DL) network could be used to perform enhanced interpolation of the regions with coarser resolution to achieve resolution enhancement (e.g., achieving super resolution in the coarse resolution areas). Through using the DL network to enhance the resolution only after the projection data has been transmitted across the slip ring, there is no increase required for the communication bandwidth. That is, the enhanced resolution can be achieved independently from the communication throughput requirements.

The trade-off between resolution and cost and the advantages of the apparatus and methods described herein can be better understood by considering that multi-slice CT scanners with large number of slices are desirable because they can image large regions of the body in one rotation. The temporal resolution of a system is limited by the data transfer rate between detector elements (DAS) and the image-reconstruction hardware (i.e., the stationary part of the CT system). The number of elements is a significant factor in determining the maximum data transfer rate. The larger the number of elements in the X-ray detector, the more challenging it is to transfer all of the data being generated across the slip ring. This can result in fewer projection images being transferred with respect to time, corresponding to a lower temporal resolution. Additionally, the cost of the CT scanner is influenced by the number of detector elements. A larger number of elements results in a more expensive scanner.

For certain applications, such as cardiac imaging with a beating heart, a high temporal resolution is desired to minimize motion artifacts. However, reducing the cost of the system is also desirable. Thus, from both image quality and cost perspectives, it is desirable to design a scanner with an overall lower number of detector elements. A multi-resolution detector can keep the total number of detector elements small, without sacrificing spatial resolution where finer resolution provides the greatest benefit. For example, in cardiac imaging, a FOV covering the entire width of the chest can be important to avoid truncation artifacts, but the regions outside of the heart do not need to be imaged with a fine resolution. Thus, the CT scanner described herein can include a multi-resolution detector having a fine pixel pitch near the center of the FOV and a coarse pixel pitch in the periphery of the FOV.

Referring now to the drawings, wherein like reference numerals designate identical or corresponding parts throughout the several views, FIG. 1 illustrates an example embodiment of a medical-imaging system 40. The medical-imaging system 40 includes at least one scanning device 100; one or more image-generation devices 150, each of which is a specially-configured computing device (e.g., a specially-configured desktop computer, a specially-configured laptop computer, a specially-configured server); and a display device 160.

The scanning device 100 is configured to acquire scan data by scanning a region (e.g., area, volume, slice) of an object (e.g., a patient). The scanning modality may be, for example, X-ray radiography. The scanning device 100 can acquire projection data of X-rays through the patient.

The one or more image-generation devices 150 obtain scan data from the scanning device 100 and generate an image of the region of the object based on the scan data. Various methods can be used to reconstruct CT images from projection data, including filtered back-projection (FBP) and statistical iterative reconstruction (IR) algorithms. Compared to more conventional FBP reconstruction methods, IR methods can provide improved image quality at reduced radiation doses. Various iterative reconstruction (IR) methods exist.

One common IR method performs unconstrained (or constrained) optimization to find the argument p that minimizes the expression $$\arg\min_{p} \{\|p - \ell\|_W^2 + \beta U(p)\},$$

wherein $\ell$ is the projection data representing the logarithm of the X-ray intensity of projection images taken at a series of projection angles and p is a reconstructed image of the X-ray attenuation for voxels/volume pixels (or two-dimensional pixels in a two-dimensional reconstructed image) in an image space. For the system matrix A, each matrix value $a_{ij}$ (i being a row index and j being a column index) represents an overlap between the volume corresponding to voxel $p_j$ and the X-ray trajectories corresponding to projection value $\ell_i^1$. The data-fidelity term $\|Ap - \ell\|_W^2$ is minimized when the forward projection A of the reconstructed image p provides a good approximation to all measured projection images $\ell$. Thus, the data fidelity term is directed to solving the system matrix equation $Ap = \ell$, which expresses the Radon transform (i.e., projections) of various rays from a source through an object OBJ in the space represented by p to X-ray detectors generating the values of $\ell$ (e.g., X-ray projections through the three-dimensional object OBJ onto a two-dimensional projection image $\ell$).

The notation $\|g\|_W^2$ signifies a weighted inner product of the form $g^T W g$, wherein W is the weight matrix (e.g., expressing a reliability of trustworthiness of the projection data based on a pixel-by-pixel signal-to-noise ratio). In other implementations, the weight matrix W can be replaced by an identity matrix. When the weight matrix W is used in the data fidelity term, the above IR method is referred to as a penalized weighted least squares (PLWS) approach.

The function U(p) is a regularization term, and this term is directed at imposing one or more constraints (e.g., a total variation (TV) minimization constraint) which often have the effect of smoothing or denoising the reconstructed image. The value β is a regularization parameter is a value that weights the relative contributions of the data fidelity term and the regularization term.

Returning to FIG. 1, after the one or more image-generation devices 150 generate the image, the one or more image-generation devices 150 send the image to the display device 160, which displays the image.

Figure 2:
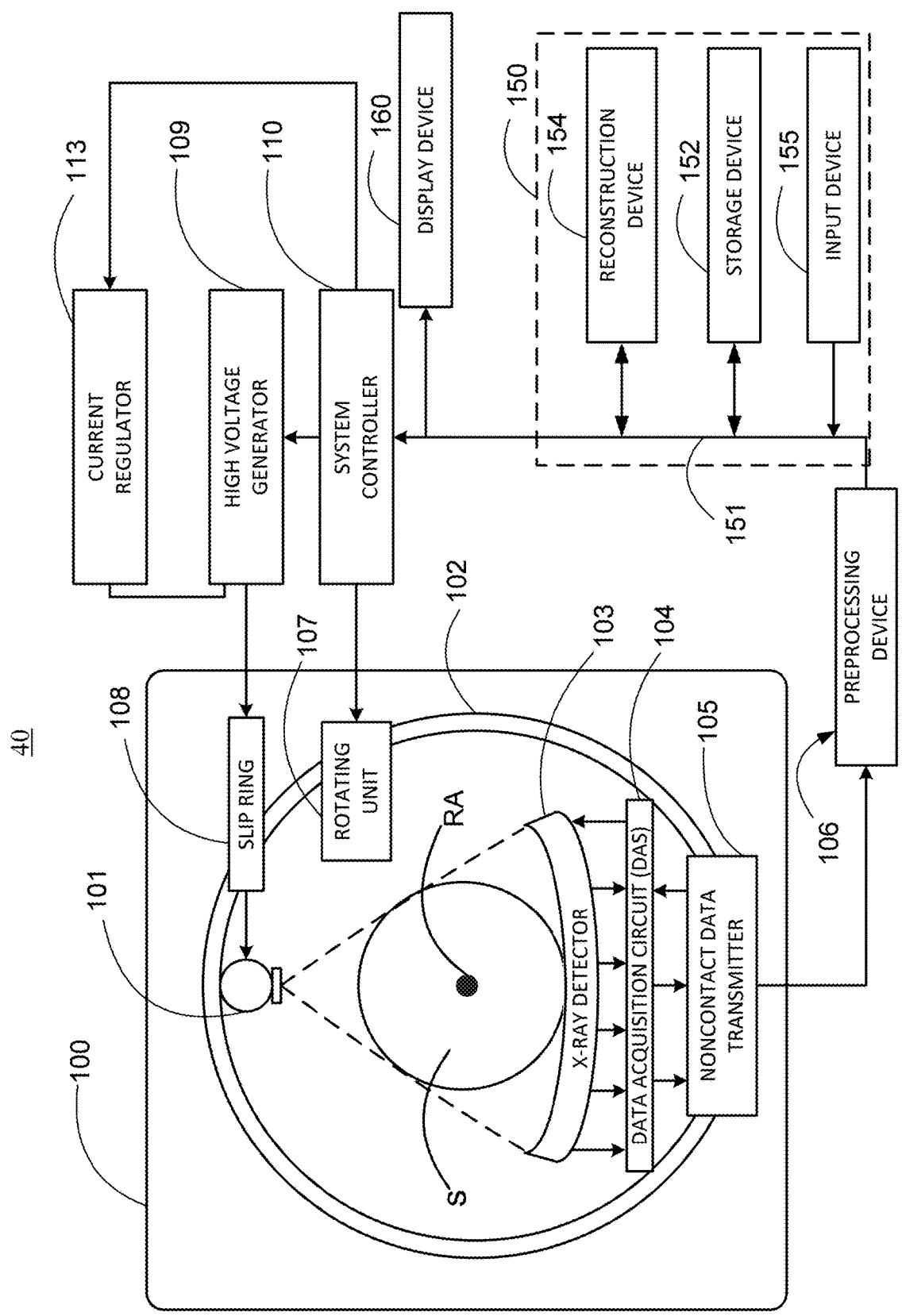
FIG. 2 shows another schematic diagram of the X-ray CT system, according to one implementation.

FIG. 2 illustrates a second implementation of the radiography gantry included in a CT scanner system 40. As shown in FIG. 2, a radiography gantry 100 is illustrated from a side view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA.

The multi-slice X-ray CT apparatus further includes a high voltage generator 109 that generates a tube voltage applied to the X-ray tube 101 through a slip ring 108 so that the X-ray tube 101 generates X-rays. The X-rays are emitted towards the object OBJ, whose cross sectional area is represented by a circle. For example, the X-ray tube 101 having an average X-ray energy during a first scan that is less than an average X-ray energy during a second scan. Thus, two or more scans can be obtained corresponding to different X-ray energies. The X-ray detector 103 is located at an opposite side from the X-ray tube 101 across the object OBJ for detecting the emitted X-rays that have transmitted through the object OBJ. The X-ray detector 103 further includes individual detector elements or units.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal.

The above-described data is sent to a preprocessing circuitry 106, which is housed in a console outside the radiography gantry 100 through a non-contact data transmitter 105 (e.g., a slip ring). The preprocessing circuitry 106 performs certain corrections, such as sensitivity correction on the raw data.

The image-generation devices 150 includes, e.g., a data/control bus 111, a storage 152, a reconstruction device 154, and an input interface 155. The storage 152 stores the resultant data, which is also called projection data at a stage immediately before reconstruction processing. The storage 152 is connected to a system controller 110 through a data/control bus 111, together with a reconstruction device 154, input interface 155, and display 160. The system controller 110 controls a current regulator 113 that limits the current to a level sufficient for driving the CT system.

The storage 152 can store the measurement value representative of the irradiance of the X-rays at the X-ray detector unit 103. Further, the storage 152 can store a dedicated program for executing method 70, which is described below with reference to FIG. 7.

The reconstruction circuitry 154 can execute various steps of method 70. Further, reconstruction circuitry 154 can execute pre-reconstruction processing image processing such as volume rendering processing and image difference processing as needed.

The pre-reconstruction processing of the projection data performed by the preprocessing circuitry 106 can include correcting for detector calibrations, detector nonlinearities, and polar effects, for example. Further, the pre-reconstruction processing can implement various steps of method 70. For example, method 70 can include processing projection data using a deep learning (DL) network to enhance resolution and/or to reduce noise and artifacts.

Post-reconstruction processing performed by the reconstruction circuitry 154 can include filtering and smoothing the image, volume rendering processing, and image difference processing as needed. The image reconstruction process can implement various steps of method 70. The reconstruction circuitry 154 can use the memory to store, e.g., projection data, reconstructed images, calibration data and parameters, and computer programs.

The reconstruction circuitry 154 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 152 can be non-volatile, such as ROM, EPROM, EEPROM or FLASH memory. The storage 152 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction circuitry 154 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 160. The display 160 can be an LCD display, CRT display, plasma display, OLED, LED or any other display known in the art.

The storage 152 can be a hard disk drive, CD-ROM drive, DVD drive, FLASH drive, RAM, ROM or any other electronic storage known in the art.

Figure 3:
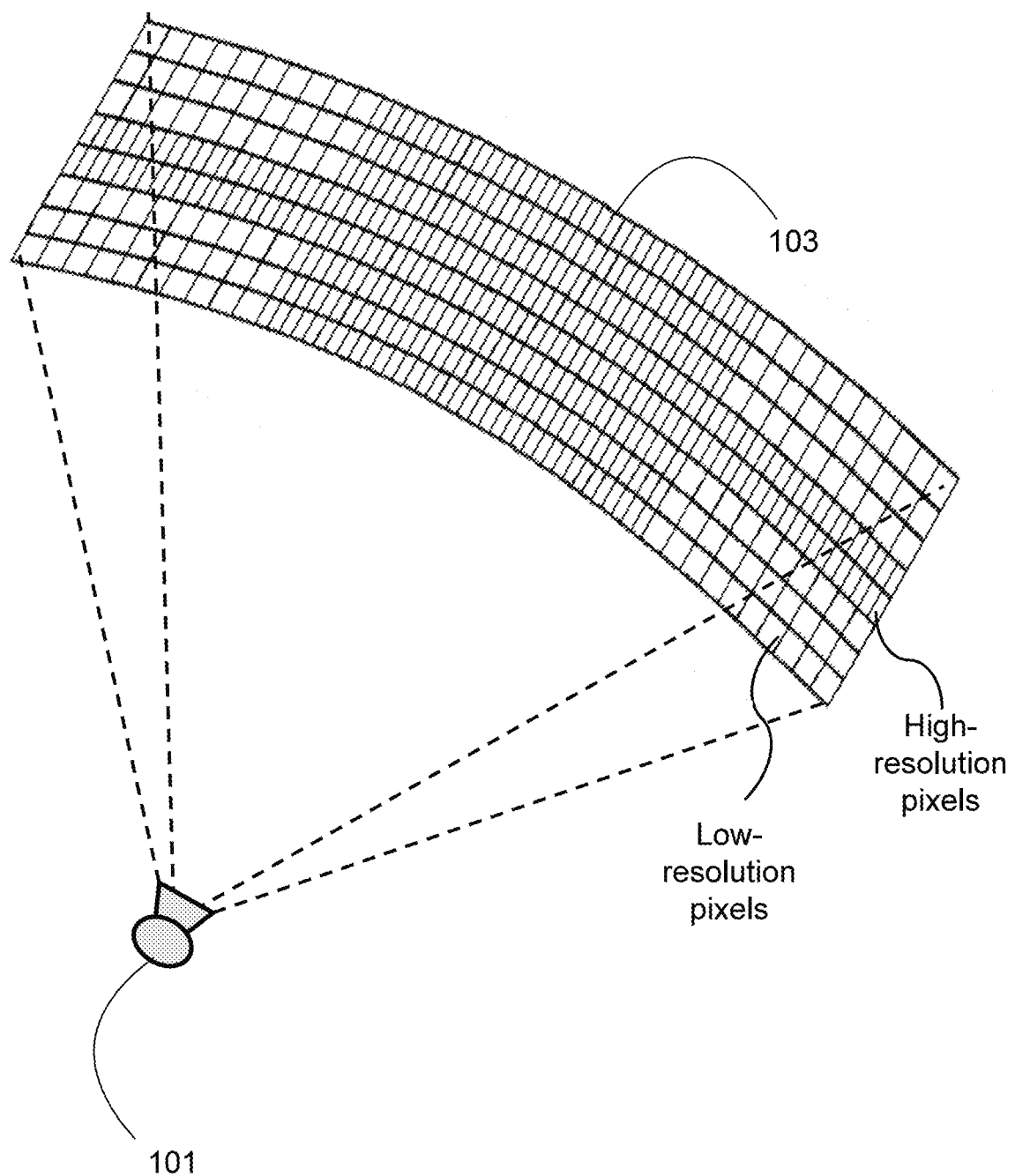
FIG. 3 shows a perspective view of an X-ray source together with a multi-resolution detector, according to one implementation.
Figure 4A:
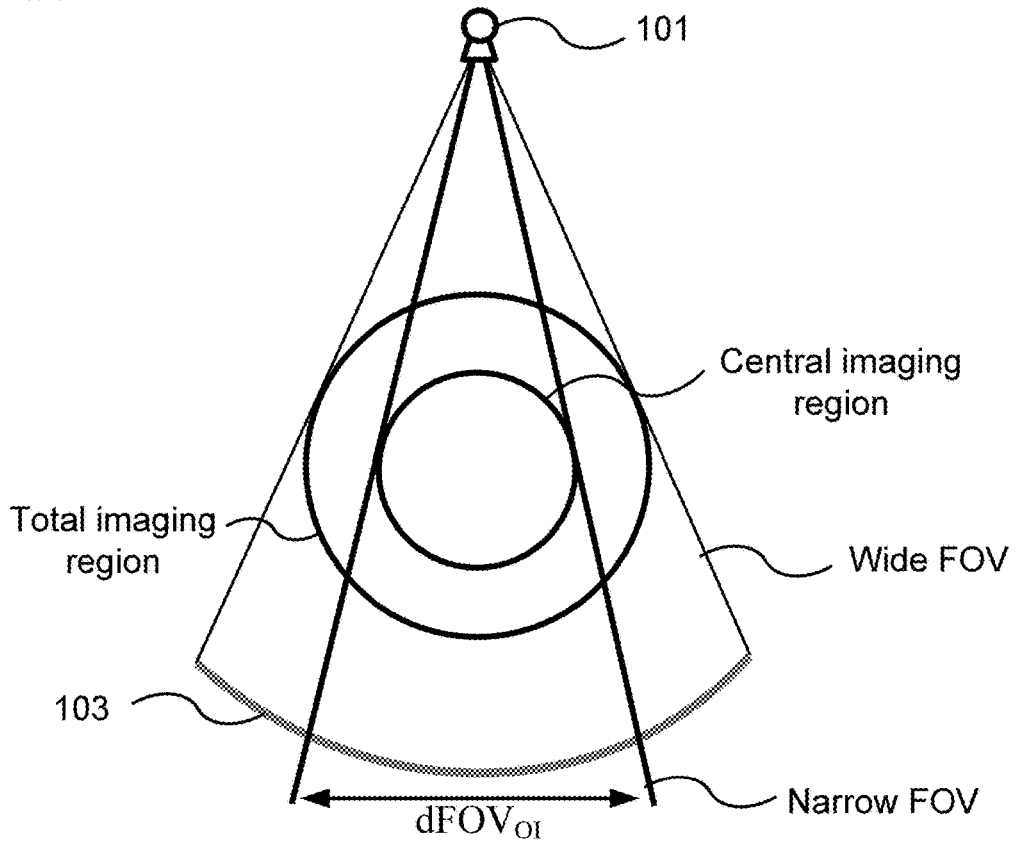
FIG. 4A shows a side view of the X-ray source together with a plus-sign multi-resolution detector, according to one implementation.
Figure 4B:
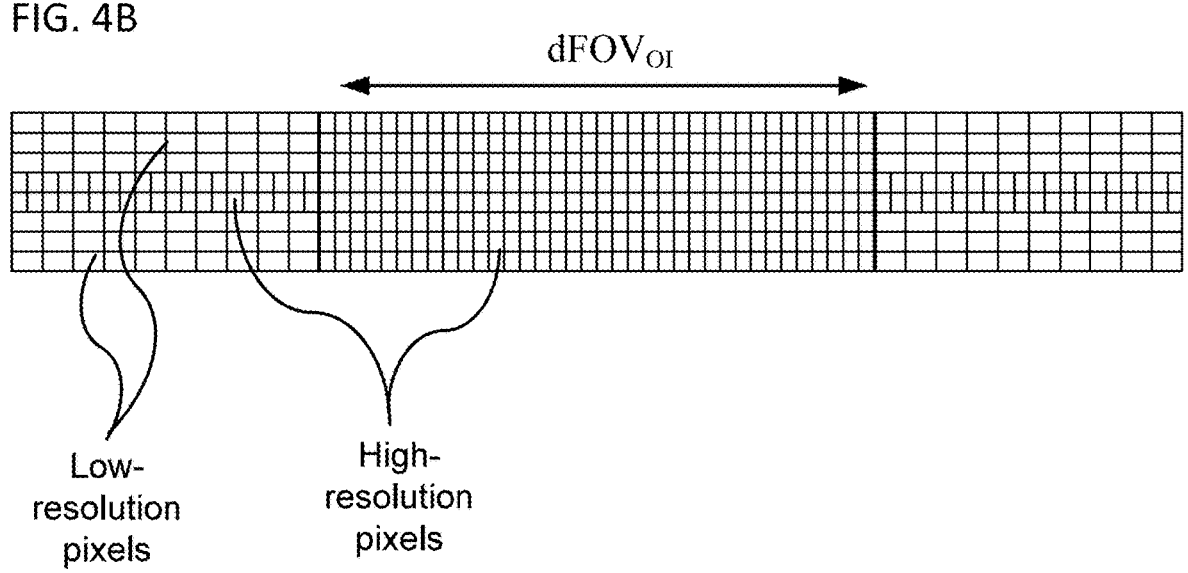
FIG. 4B shows a pixel configuration of the plus-sign multi-resolution detector, according to one implementation.

FIG. 3 shows a prospective view of the X-ray source 101 together with the detector 103 in which the high-resolution pixels are configured in a plus shape, and the low-resolution pixels are configured in the peripheral parts of the detector 103 in which the high-resolution pixels are absent (i.e., the four corners. FIG. 4A shows a side view of the X-ray source 101 together with the detector 103. FIG. 4B shows the plus-sign-shaped pattern for the high-resolution pixels on the detector 103. FIG. 4A shows that the total imaging region can be divided into a central imaging region and a peripheral region, which is mutual exclusive from the central region. The central region can include the object of interest, and higher resolution can be desired for imaging the central region. Thus the pixels in the narrow FOV can have a higher resolution than pixels in the peripheral FOV (i.e., the peripheral FOV is the portion of the total, wide FOV that is outside of the narrow FOV). The narrow FOV can also be referred to as the small FOV, and can be represented as $dFOV_{OI}$.

Thus, in applications such as cardiac scanning, the object of interest (e.g., heart) lies within a relatively small field of view $dFOV_{OI}$. To avoid truncation artifacts, objects outside of $dFOV_{OI}$ should still be sampled. Since objects outside of $dFOV_{OI}$ are not part of the main image, they can be sampled with a larger pixel size (i.e., lower/coarser resolution). Because larger pixels are used to cover the peripheral regions, the total number of pixels in the detector 103 can be reduced relative to a single-resolution detector in which all pixels are small. In FIG. 4B, the plus-sign-shaped configuration for the small pixels provides higher resolution along a central strip of the detector 103 in both dimensions, and the four corner regions each is covered with larger pixels.

Figure 5A:
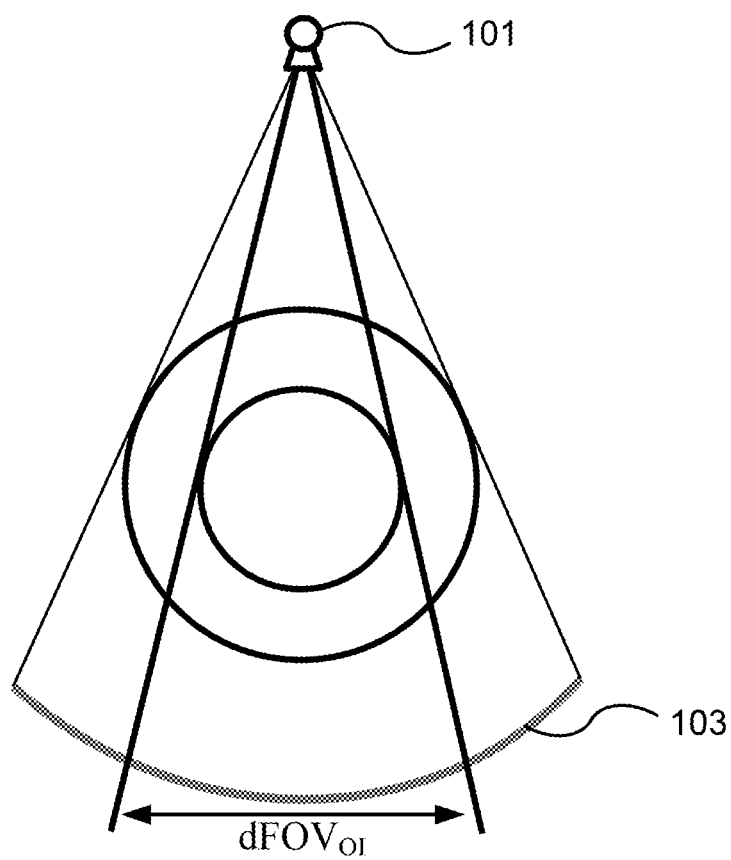
FIG. 5A shows a side view of the X-ray source together with a single-band multi-resolution detector, according to one implementation.
Figure 5B:
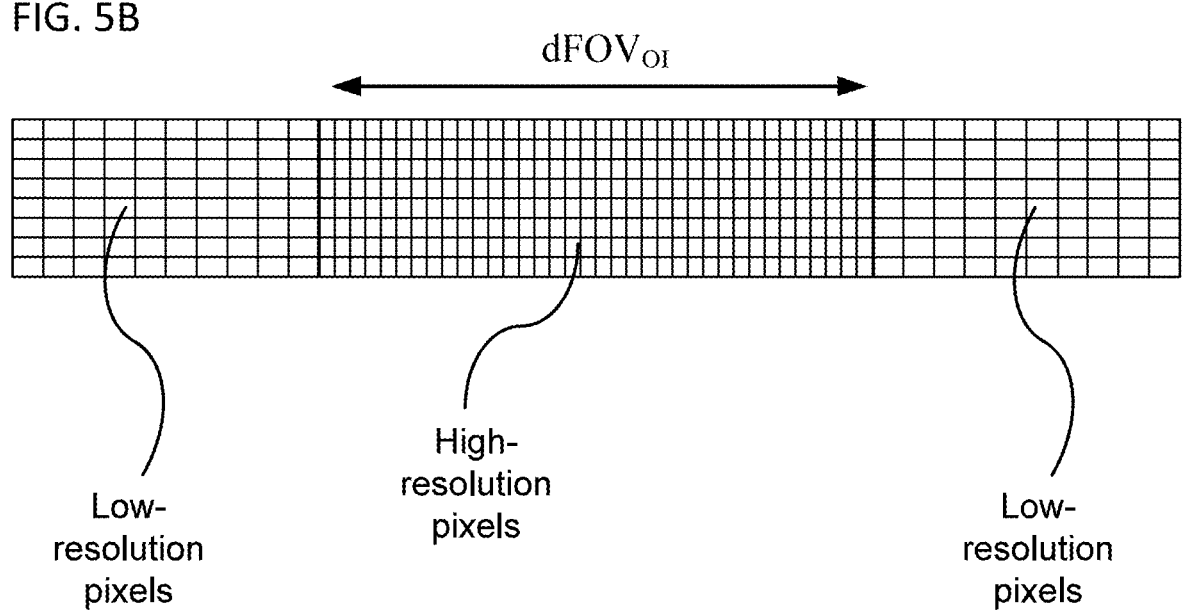
FIG. 5B shows a pixel configuration of the single-band multi-resolution detector, according to one implementation.

FIG. 5A shows a side view of the X-ray source 101 together with a single-strip detector 103, which has a uniform width for the strip of high-resolution pixels. FIG. 5B shows a configuration of the pixels of the single-strip detector 103. If the small field of view $dFOV_{OI}$, is the region having the uniform width indicated in FIGS. 5A and 5B, then the high-resolution pixels occupy all of the small field of view $dFOV_{OI}$, and none of the high-resolution pixels are found outside of the small field of view $dFOV_{OI}$. This configuration is referred to as the centered single-width configuration (also referred to as the single-width configuration).

Figure 6A:
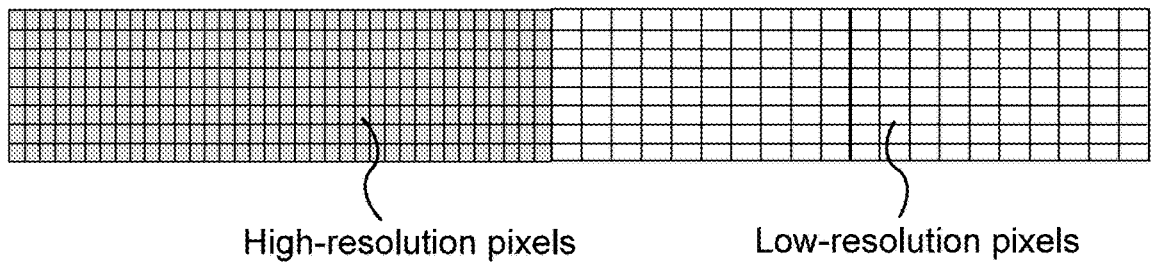
FIG. 6A shows a one-sided, single-width configuration for the pixels of the multi-resolution detector, according to one implementation.
Figure 6B:
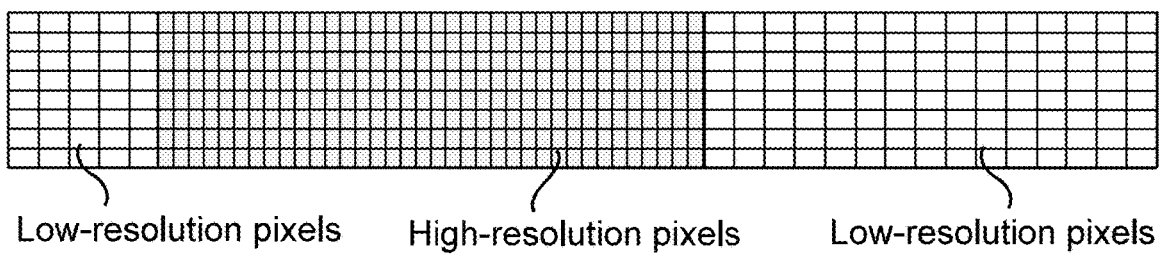
FIG. 6B shows an off-center, single-width configuration for the pixels of the multi-resolution detector, according to one implementation.
Figure 6C:
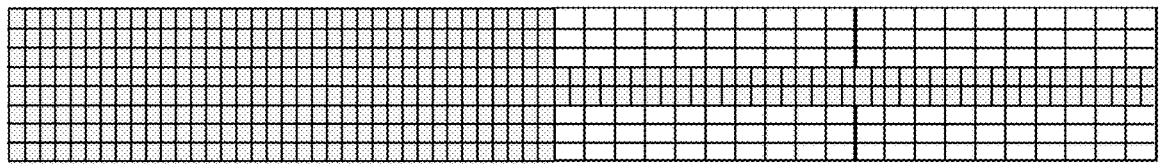
FIG. 6C shows a one-sided, plus-shape configuration for the pixels of the multi-resolution detector, according to one implementation.
Figure 6D:
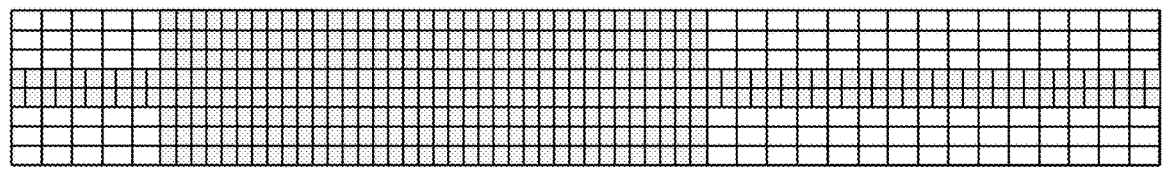
FIG. 6D shows a off-center, plus-shape configuration for the pixels of the multi-resolution detector, according to one implementation.
Figure 6E:
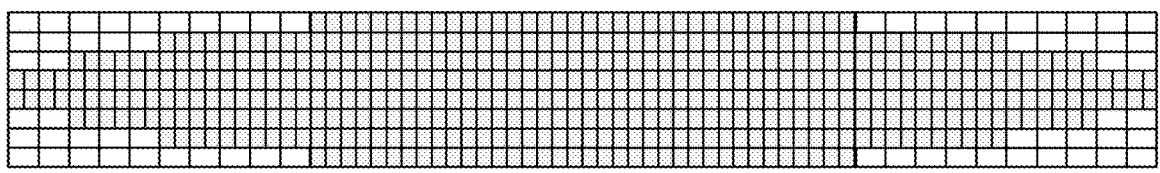
FIG. 6E shows a tapered configuration for the pixels of the multi-resolution detector, according to one implementation.

FIGS. 6A-6E show five other configurations for the high-resolution pixels. In FIG. 6A, a one-sided configuration is shown, in which one half of the detector has high-resolution pixel elements and the other half has low-resolution pixel elements. In FIG. 6B, an off-center, single-width configuration is shown. In FIG. 6C, a one-sided, plus-shape configuration is shown. In FIG. 6D, an off-center, plus-shape configuration is shown. In FIG. 6E, a tapered configuration is shown. Variations of these configurations for the high-resolution pixels can be used without departing from the spirit of the disclosure, as would be understood by a person of ordinary skill in the art.

Figure 7:
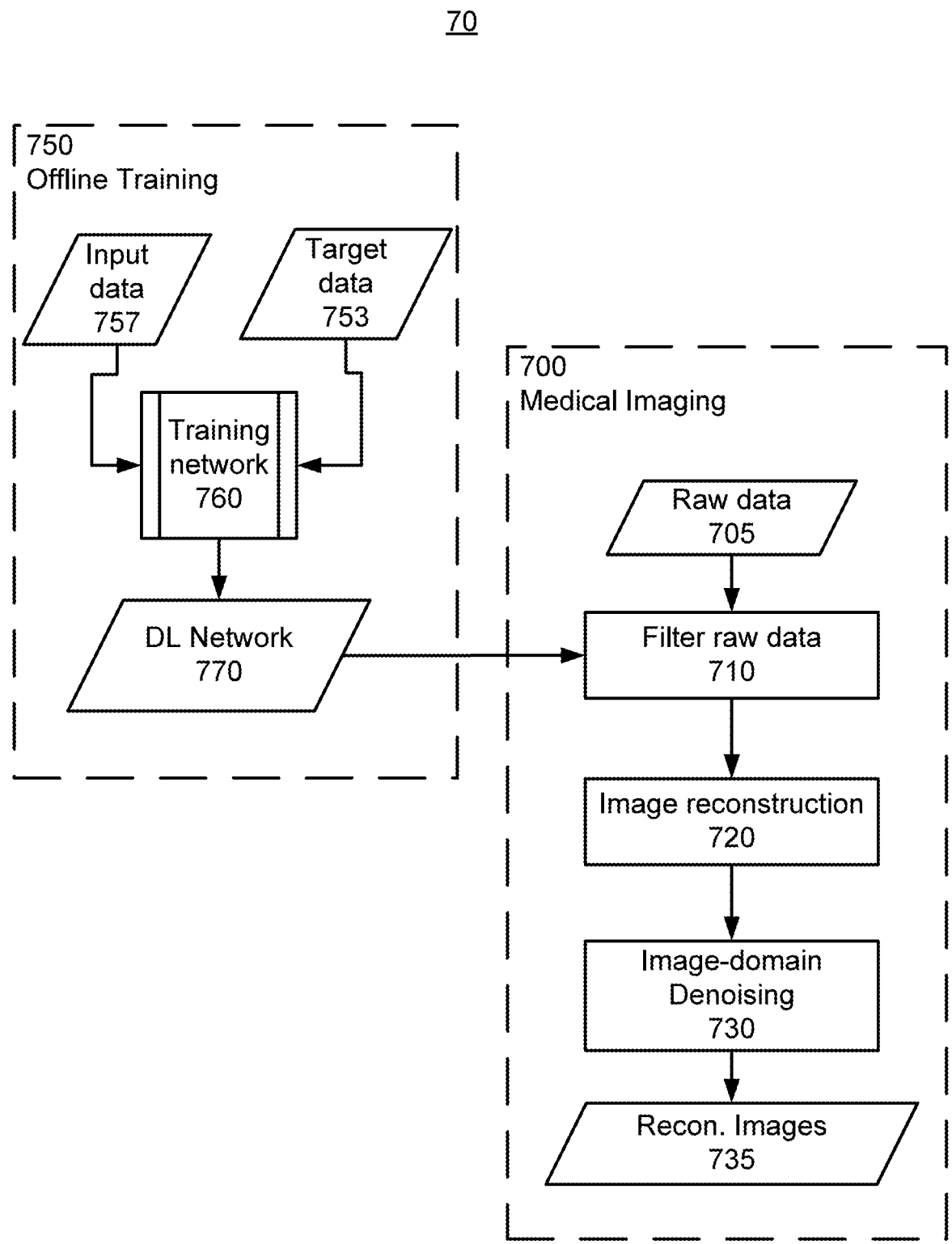
FIG. 7 shows a flow diagram of a method of training a deep learning (DL) network and then using the DL network to enhance the resolution of projection data acquired using a multi-resolution detector, according to one implementation.

FIG. 7 shows a method 70 of training a deep learning (DL) network 770 to perform a smart interpolation of the projection data obtained using a multi-resolution detector, such as those illustrated in FIGS. 4B, 5B, and 6A-6E to achieve a higher resolution in the regions of the projection data corresponding to the larger pixels in the multi-resolution detector 103. Thus, the filtered projection data output from the DL network 770 can have a uniform pixel pitch (e.g., the pixel values can be on a uniform grid).

FIG. 7 shows a flow diagram for a non-limiting example of a method 70 that trains and uses a DL neural network 770 to perform data-domain corrections to X-ray projection data (e.g., edge/resolution enhancement, sinogram restoration, denoising, and/or artifact correction). Method 70, as illustrated in FIG. 7, uses the DL network 770 to learn how to optimal filter raw data 705 (e.g., a sinogram), and then reconstructs a CT image from the filtered sinogram. Method 70 includes two parts: (i) an offline training process 750 and (ii) a medical imaging process 700. That is, process 750 trains the DL network 770, and process 700 uses the trained DL network 770 to filter the raw data 705 in the projection domain, thereby generating high-quality sinograms having a higher resolution than the raw data, especially in regions corresponding to larger pixels. In certain implementations such as fluoroscopy, steps 720 and 730 can be omitted and the output can be the corrected projection data.

In certain implementations, the network 770 is a convolutional neural network (CNN) in which series of convolution, batch normalization, and rectified linear unit network layers are performed.

The network 770 is trained using process 760. In process 760, a loss function is used to iteratively adjust/optimize parameters of the DL network 770 (e.g., the parameters of the DL network 770 can include weighting coefficients connecting network layers, and activation functions/potentials of nodes within the layers). The optimization of the network parameters continues until stopping criteria are satisfied (e.g., a stopping criterion can be whether the value of the loss function converged to a predefined threshold) to generate the trained network 770.

The loss function compares target data 753 to an output generated by applying the input data 757 to a current version of the DL network 770. For example, the input data can be projection data acquired using a multi-resolution detector configuration, and the target data can be projection data acquired using a uniform high-resolution detector configuration.

For a given CT scan, each low-quality sinogram of the input data (e.g., sinograms acquired using a multi-resolution detector) forms a pair with the corresponding high-quality sinogram (e.g., sinograms acquired using a uniform high-resolution detector). The scans to acquire the low-quality sinograms for the input data 757 and the high-quality sinograms for the target data 753 can be performed on a phantom, for example. Additionally, the DL network 770 can be trained to perform denoising and artifact reduction in addition to resolution enhancement by, e.g., acquiring the low-quality sinograms suing a lower dose than is used to acquire the high-quality sinograms.

Applying a low-quality sinogram from the input data to the current version of the DL network 770 generates an output from the network that is supposed to be a resolution-enhanced version of the low-quality sinogram (i.e., a filtered sinogram). The DL network 770 is trained by iteratively adjusting the network coefficients in the DL network 770 to minimize the difference between the Filtered sinogram output from the network 770 and the high-quality sinogram from the target data 753. The training of the network 770 is determined to be complete when the difference is minimized between the target data and the output from the DL network 770. The question of whether or not this difference has been sufficiently minimized is resolved based on one or more predetermined stopping criteria of the process 760. Once the stopping criteria have been satisfied, the trained network 770 can then be stored and then later recalled to be used in the medical imaging process 700.

In alternative implementations, the DL network 770 is implemented as a residual network (ResNet). In this case, the method described herein can filter an image by treating the difference between the low- and high-quality sinograms as an additive residue that can be directly removed from the low-quality sinogram. Thus, when a low-quality sinogram is applied to the neural network, the network outputs an image corresponding to the difference image. Then the corrected sinogram can be generated by subtracting the network output (the noise/artifact) from the low-quality sinogram to generate the corrected sinogram.

In process 760 of method 70, a loss function is used to iteratively adjust network coefficients (e.g., weights and biases of convolutional and pooling layers) of the DL network 770 until stopping criteria are satisfied (e.g., convergence of the parameters to a predefined threshold) to generate the trained network 770. The loss function compares high-quality data 753 to results of a current version of the DL network 770 to which input data 757 is applied.

Process 700 is performed by obtaining raw data 705, e.g., by performing a CT scan to generate CT projections at a series of view angles (i.e., a low-quality sinogram). For example, the sinogram can be performed using a low-dose CT scan to generate the raw data 705.

In step 710 of process 700, the raw data 705 is filtered by applying the raw data 705 to the trained DL network 770. The DL network 770 then outputs a Filtered sinogram. In certain implementations, the DL network 770 is a convolution neural network (CNN). The CNN can be a network that directly generates local small sized filters, e.g., $$y_i = \sum_{j \in Neighbor\ of\ i} w_{ij} x_j$$

wherein $w_{ij}$ is the filter on the ith pixel.

In the training process 760, the same process as used in step 710 to generate the filtered sinograms from the raw data 705 is also used to generate output sinograms from the input data, and then compare, using the loss function, the output sinograms to the target data.

In step 720 of process 700, a CT image is reconstructed from the denoised sinogram. Various methods can be used to reconstruct CT images from projection data, including filtered back-projection (FBP) and statistical iterative reconstruction (IR) algorithms. In addition to FBP, other analytical methods can be used such as the Feldkamp Davis Kress (FDK) method Adaptive Iterative Dose Reduction 3D (AIDR 3D) method. Compared to FBP reconstruction methods, IR methods can provide improved image quality at reduced radiation doses. In one example, an IR method is performed by solving the optimization problem $$\arg\min_{p} \{\|p - \ell\|_W^2 + \beta U(p)\},$$

as discussed above.

In step 730 of process 700, additional image-domain denoising is performed. This step is optional, and can be omitted in some implementations.

Example denoising methods include linear smoothing filters, anisotropic diffusion, non-local means, or nonlinear filters. Linear smoothing filters remove noise by convolving the original image with a convolution kernel that represents a low-pass filter or smoothing operation. For example, a Gaussian convolution kernel comprises elements determined by a Gaussian function. This convolution brings the value of each pixel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels using a weighted average over similar patches within the images.

Finally, a reconstructed image 735 is output having good image quality, and the reconstructed image 735 can be displayed to a user or stored for later use.

Now a more detailed description of training a DL network is provided (e.g., process 760). Here, the target data 753 are high-quality sinograms acquired using a uniform high-resolution detector, and the input data 757 are low-quality sinograms acquired using a multi-resolution detector, as described above.

Figure 8:
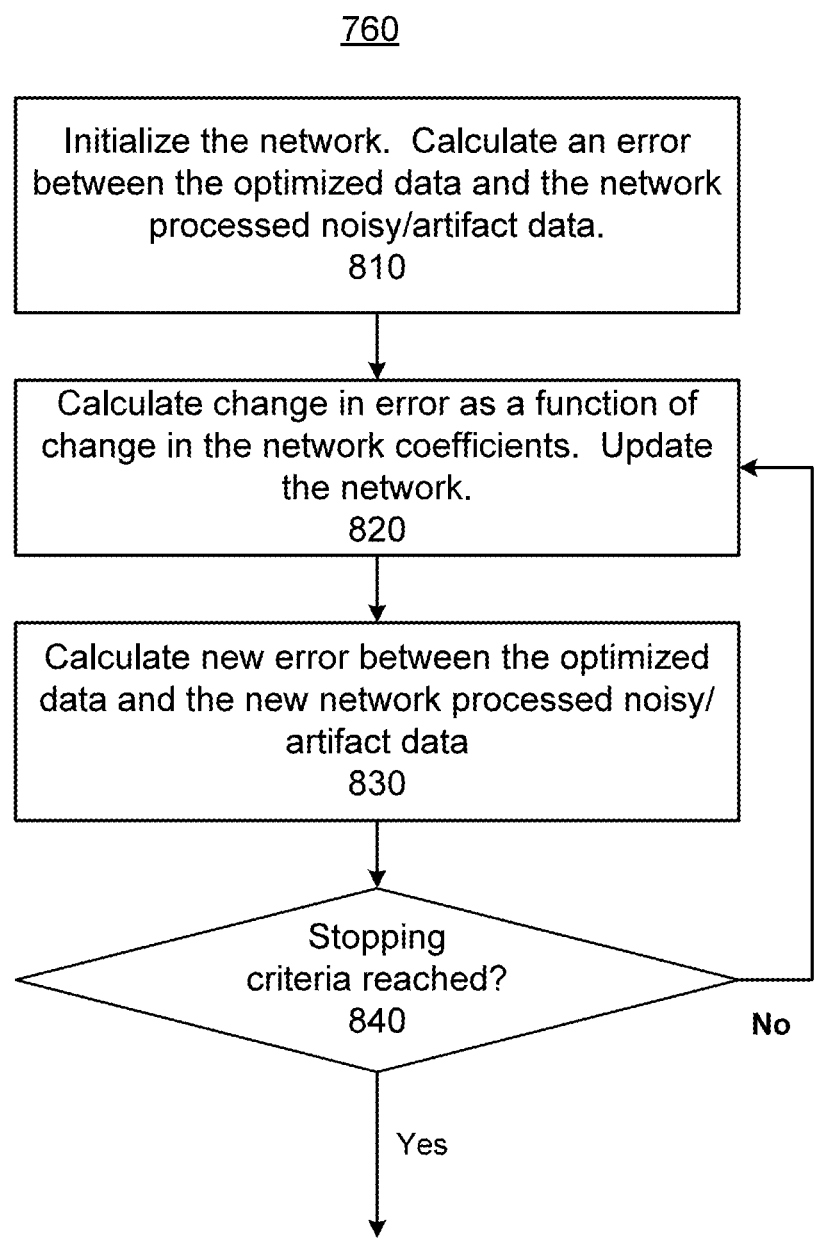
FIG. 8 shows a flow diagram of the process to train the DL network by iteratively adjusting coefficients of the DL network to optimize a loss function, according to one implementation.

FIG. 8 shows a flow diagram of one implementation of the training process 760. In process 760, input data 757 and target data 753 are used as training data to train a DL network 770, resulting in the DL network 770 being output from step 840 of process 760. The offline DL training process 760 trains the DL network 770 using a large number of input sinograms 757 that are paired with corresponding target sinograms 753 to train the DL network 770 to produce, from the input sinograms 757, filtered sinograms resembling the target sinograms 753.

In process 760, a set of training data is obtained, and the network 770 is iteratively updated to reduce the error (e.g., the value produced by a loss function). The DL network infers the mapping implied by the training data, and the cost function produces an error value related to the mismatch between the target sinograms 753 and the result produced by applying a current incarnation of the DL network 770 to the input sinograms 757. For example, in certain implementations, the cost function can use the mean-squared error to minimize the average squared error. In the case of a of multilayer perceptrons (MLP) neural network, the back-propagation algorithm can be used for training the network by minimizing the mean-squared-error-based cost function using a (stochastic) gradient descent method.

In step 810 of process 760, an initial guess is generated for the coefficients of the DL network 770. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 810 through 840 of process 760 provide a non-limiting example of an optimization method for training the DL network 770.

An error is calculated (e.g., using a loss function or a cost function) to represent a measure of the difference (e.g., a distance measure) between the target sinograms 753 (i.e., ground truth) and input sinograms 757 after applying a current version of the network 770. The error can be calculated using any known cost function or distance measure between the image data, including those cost functions described above. Further, in certain implementations the error/loss function can be calculated using one or more of a hinge loss and a cross-entropy loss. In certain implementations, the loss function can be the $\ell_p$-norm of the difference between the target data and the result of applying the input data to the DL network 770. Different values of "p" in the $\ell_p$-norm can be used to emphasize different aspects of the noise. Further, a weighting mask (e.g., based on the attenuation coefficient of signal intensity) can be applied on a pixel-by-pixel basis to the difference between the target data and the result generated from the input data. In certain implementations, rather than minimizing an $\ell_p$-norm of the difference between the target data and the result from the input data, the loss function can represent a similarity (e.g., using a peak signal-to-noise ratio (PSNR) or a structural similarity (SSIM) index).

In certain implementations, the training is performed by minimizing the following loss function $$\hat{\theta} = \arg\min_{\theta} \frac{1}{N} \sum_n L(\bar{y}^{(n)}, f(y^{(n)} \mid \theta, h)) + \beta R(h)$$

where θ are the adjustable weighting coefficients of the DL network 770, h are the non-adjustable parameters (e.g., parameters selected by a user, such as the choice of reconstruction kernel), $y^{(n)}$ represents the nth input sinogram, $\bar{y}^{(n)}$ represents the nth target sinogram. The number N is the total number of training projections. In certain implementations, the following weighted mean absolute error loss function is used $$L(\bar{y}, y) = \sum_j d_j |y_j - \bar{y}_j|$$

wherein $d_j$ is the weight which has the form $$d_j = \bar{y}_j^p$$

with p being a scalar. The choice of this weight is inspired by the statistical mean estimation method where $d_j$ is often necessarily chosen to be the inverse of data noise variance. To handle the overfitting issue an additional regularization R on h is used, which is given by R $(h)=\Sigma_j h_j$. The regularization strength can be tuned thru the parameter $\beta$.

In certain implementations, the network 770 is trained using backpropagation. Backpropagation can be used for training neural networks and is used in conjunction with gradient descent optimization methods. During a forward pass, the algorithm computes the network's predictions based on the current parameters $\theta$. These predictions are then input into the loss function, by which they are compared to the corresponding ground truth labels (i.e., the high-quality target data 753). During the backward pass, the model computes the gradient of the loss function with respect to the current parameters, after which the parameters are updated by taking a step of size of a predefined size in the direction of minimized loss (e.g., in accelerated methods, such that the Nesterov momentum method and various adaptive methods, the step size can be selected to more quickly converge to optimize the loss function).

The optimization method by which the backprojection is performed can use one or more of gradient descent, batch gradient descent, stochastic gradient descent, and mini-batch stochastic gradient descent. The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to FIG. 8, step 820 of process 760 determines a change in the error as a function of the change in the network can be calculated (e.g., an error gradient), and this change in the error can be used to select a direction and step size for a subsequent change to the weights/coefficients of the DL network 770. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 820 of process 760, a new set of coefficients are determined for the DL network 770. For example, the weights/coefficients can be updated using the changed calculated in step 820, as in a gradient descent optimization method or an over-relaxation acceleration method.

In step 830 of process 760, a new error value is calculated using the updated weights/coefficients of the DL network 770.

In step 840, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in process 760 will continue back to the start of the iterative loop by returning and repeating step 820 using the new weights and coefficients (the iterative loop includes steps 820, 830, and 840). When the stopping criteria are satisfied the training process performed in process 760 is completed.

Figure 9:
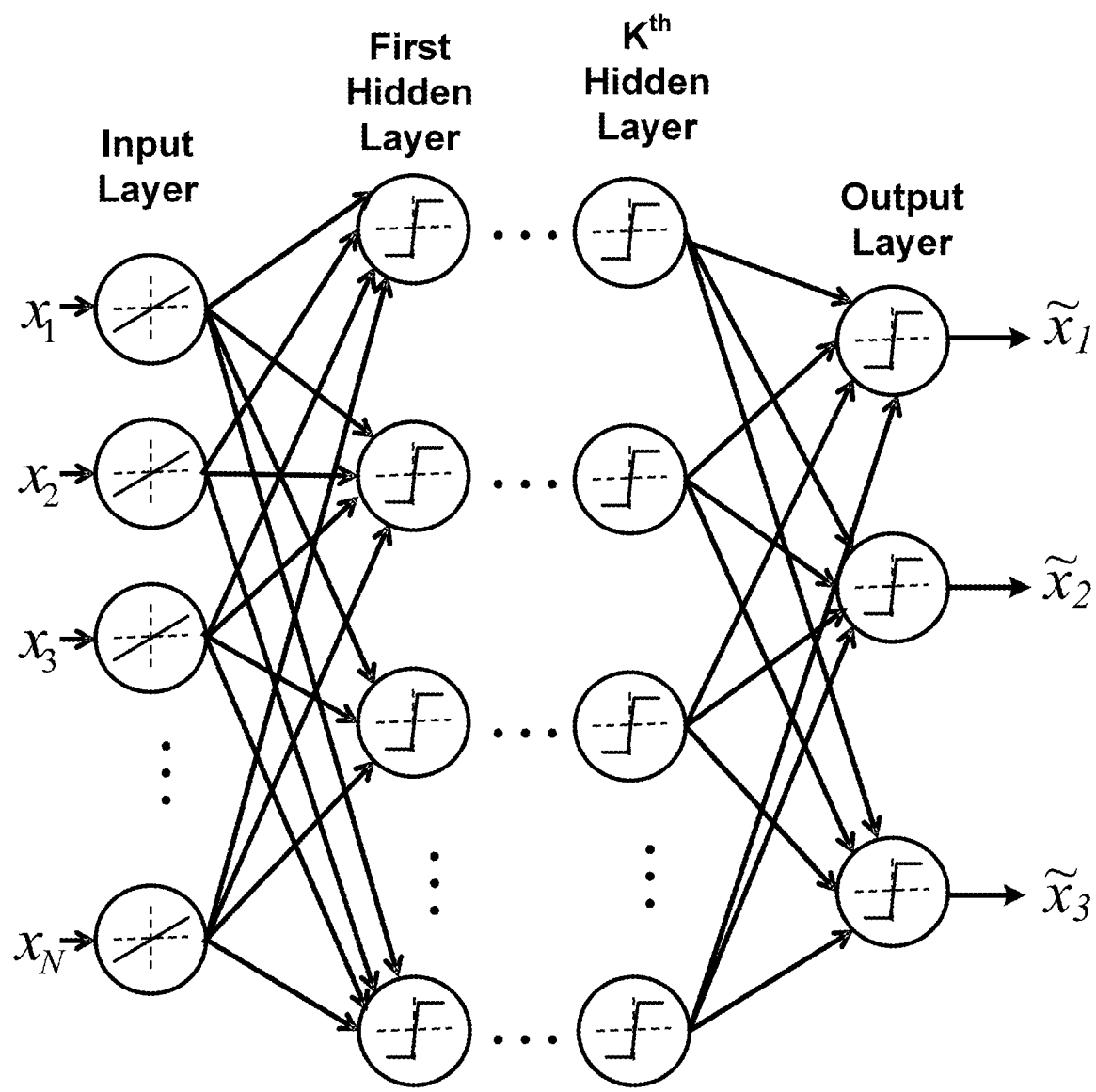
FIG. 9 shows an example of a DL network, according to one implementation.
Figure 10:
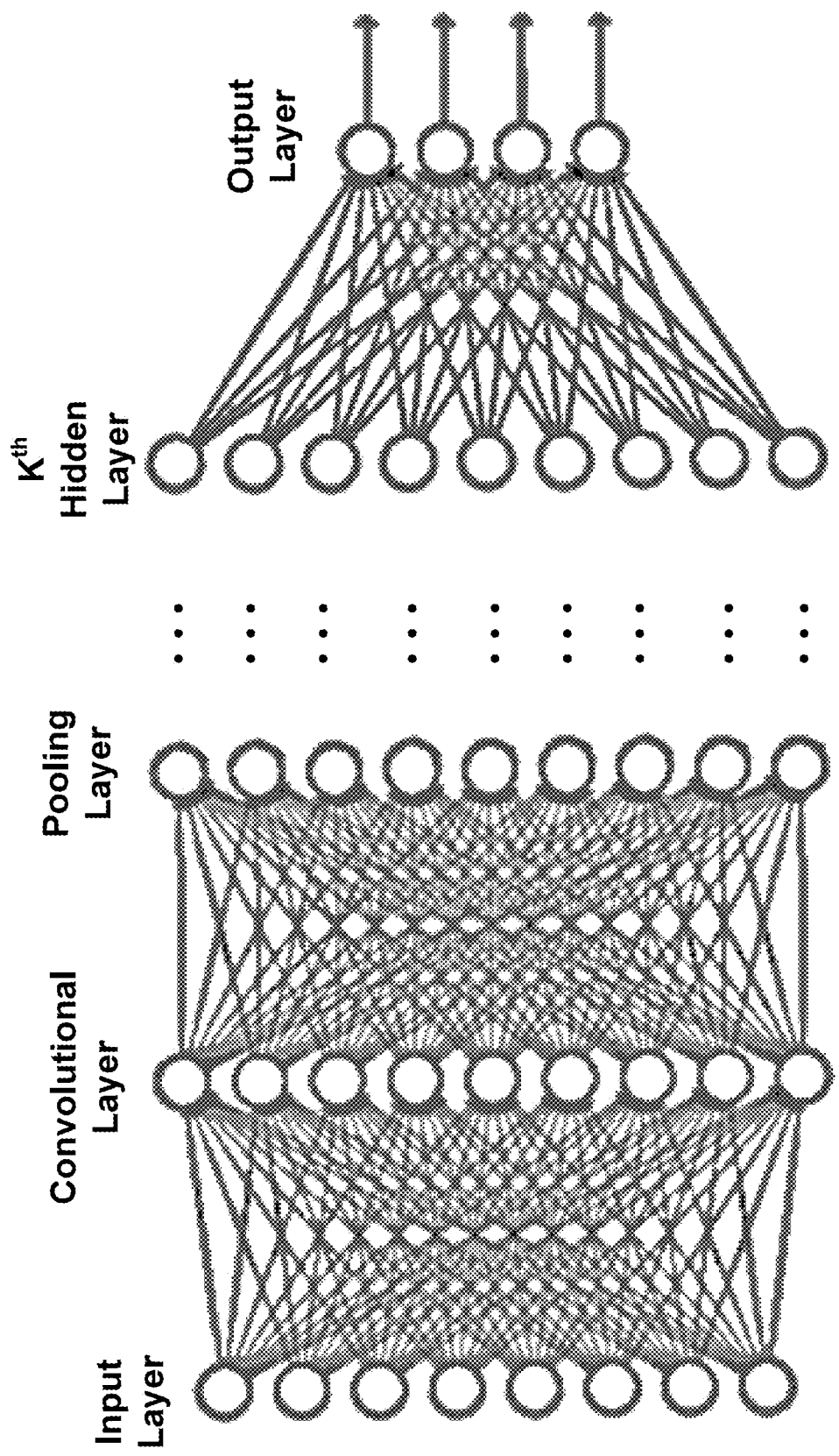
FIG. 10 shows an example of the DL network being a convolutional neural network (CNN), according to one implementation.

FIGS. 9 and 10 show two examples of the inter-connections between layers in the DL network 770. The DL network 770 can include fully connected, convolutional, and the pooling layer, all of which are explained below. In certain preferred implementations of the DL network 770, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL network 770 can also incorporate batch normalization, as also exemplified in the first and second examples discussed above.

FIG. 9 shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIG. 9. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 9 (and similarly in FIG. 10), the neurons (i.e., nodes) are depicted by circles around a threshold function. For the non-limiting example shown in FIG. 9, the inputs are depicted as circles around a linear function, and the arrows indicate directed connections between neurons. In certain implementations, the DL network 770 is a feedforward network.

FIG. 10 shows a non-limiting example in which the DL network 770 is a convolutional neural network (CNN). CNNs are type of ANN that has beneficial properties for image processing, and, therefore, have specially relevancy for the applications of image denoising. CNNs use feedforward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
circuitry configured to
obtain projection data representing an intensity of X-rays detected by a detector array comprising a plurality of pixels, the plurality of pixels including first pixels and second pixels having a larger size than the first pixels, wherein the first pixels are configured in a central portion of a field of view of an X-ray beam and the second pixels are configured in a peripheral portion arranged around the central portion,
acquire a neural network, the neural network having been trained using a training dataset including input data and target data, the input data comprising input projection data that was generated using a multi-resolution detector configuration corresponding to the plurality of pixels of the detector array, and the target data comprising target projection data that was generated using a second detector configuration having a finer resolution than a coarse-resolution part of the multi-resolution configuration, and
apply the projection data to the neural network to thereby output filtered projection data from the neural network.

2. The apparatus according to claim 1, wherein the circuitry is further configured to apply the projection data to the neural network to thereby output the filtered projection data having a uniform pixel resolution of the first pixels.

3. The apparatus according to claim 1, wherein the circuitry is further configured to acquire the neural network, and the neural network has been trained using the target data that is acquired using the second detector configuration, and the second detector configuration has a uniform pixel resolution corresponding to a pixel resolution of the first pixels of the detector array.

4. The apparatus according to claim 1, further comprising:
an X-ray source configured to emit the X-ray beam having the field of view with the central portion and the peripheral portion, and
the detector array, which is arranged across a gantry from the X-ray source to detect X-rays within the field of view of the X-ray beam.

5. The apparatus according to claim 4, wherein the detector array is further configured with the first pixels arranged in a plus-shape with a first band along a central axis of the detector array in a first direction and a second band along another central axis of the detector array in a second direction.

6. The apparatus according to claim 4, wherein the detector array is further configured with the first pixels arranged in a single band of uniform width along a first direction of the detector array.

7. The apparatus according to claim 4, Wherein the X-ray source is further configured such that the central portion of the field of view spans a region of interest and the peripheral portion of the field of view falls outside the region of interest but spans an imaging region for avoiding truncation artifacts.

8. The apparatus according to claim 4, wherein the X-ray source is further configured to emit a higher X-ray intensity in the central portion of the field of view than in the peripheral portion of the field of view.

9. The apparatus according to claim 4, wherein the detector array is a single monolithic structural member and the first pixels lie on a same surface as the second pixels.

10. The apparatus according to claim 1, wherein the circuitry is further configured to train the neural network by
obtaining the training dataset comprising input sinograms paired with respective target sinograms, the input sinograms being generated using the multi-resolution detector configuration, and the target sinograms being generated using the second detector configuration,
using the neural network to generate output sinograms from the respective input sinograms by applying a given input sinogram to the neural network, thereby generating a corresponding output sinogram, and
training the neural network by iteratively adjusting weighting coefficients of the neural network to minimize a value of a loss function, the loss function measuring a disagreement between the output sinogram and a target sinogram that corresponds to the given input sinogram used when generating the output sinogram.

11. The apparatus according to claim 10, wherein the circuitry is further configured to train the neural network, wherein the loss function includes a peak signal-to-noise ratio, a structural similarity index, and/or an $l_p$-norm of a difference between the respective target sinograms and filtered sinograms corresponding to the input sinograms.

12. The apparatus according to claim 10, wherein the circuitry is further configured to train the neural network to generate the output sinograms, wherein the output sinograms have enhanced resolution relative to the input sinograms, by training the neural network using the training dataset, wherein the second detector configuration used to acquire the target sinograms has a uniform pixel resolution corresponding to a pixel resolution of the first pixels.

13. The apparatus according to claim 1, wherein the circuitry is further configured to obtain the projection data, wherein the projection data is fluoroscopy data.

14. The apparatus according to claim 1, wherein the circuitry is further configured to obtain the projection data, wherein the projection data is a sinogram of a computed tomography (CT) scan, and
reconstruct an image from the filtered projection data.

15. The apparatus according to claim 1, wherein the circuitry is further configured to obtain projection data, wherein a configuration of the first pixels of the plurality of pixels is selected from (i) a single-sided, single-band configuration, (ii) a single-sided, plus-sign configuration, (iii) an off center, single-band configuration, (iv) an off-center, plus-sign configuration, and (v) a tapered configuration, wherein the single-sided, single-band configuration has the first pixels on one side of the detector array and the second pixels on another side of the detector array, the single-sided, plus-sign configuration has a first band of the first pixels along a first direction on the one side of the detector array and has a second band of the first pixels along a central axis in a second direction on the another side of the detector array, the off center, single-band configuration has the first band of the first pixels off of a center axis along the first direction, but not entirely to the one side of the detector array, the off center, plus-sign configuration has the first band of the first pixels off of the center axis along the first direction, but not entirely to the one side of the detector array, and has the second band of the first pixels extending to either side of the first band in the second direction, and the tapered configuration has the first pixels in a shape that tapers in the first and second directions.

16. A method, comprising:

obtaining projection data representing an intensity of X-rays detected by a detector array comprising a plurality of pixels, the plurality of pixels including first pixels and second pixels having a larger size than the first pixels, wherein the first pixels are configured in a central portion of a field of view of an X-ray beam and the second pixels are configured in a peripheral portion arranged around the central portion;

acquiring a neural network, the neural network having been trained using a training dataset including input data and target data, the input data comprising input projection data that was generated using a multi-resolution detector configuration corresponding to the plurality of pixels of the detector array, and the target data comprising target projection data that was generated using a second detector configuration having a finer resolution than a coarse-resolution part of the multi-resolution configuration; and applying the obtained projection data to the neural network to thereby output filtered projection data from the neural network.

17. The method according to claim 16, further comprising generating the projection data using an X-ray source configured to emit the X-ray beam having the field of view with the central portion and the peripheral portion, and the detector array being arranged across a gantry from the X-ray source to detect X-rays within the field of view of the X-ray beam, wherein the X-ray source is further configured to emit a higher X-ray intensity in the central portion of the field of view than in the peripheral portion of the field of view.

18. The method according to claim 16, further comprising training the neural network by obtaining the training dataset comprising input sinograms paired with respective target sinograms, the input sinograms being acquired using the multi-resolution detector configuration, and the target sinograms being using the second detector configuration, using the neural network to generate output sinograms from the respective input sinograms by applying a given input sinogram to the neural network, thereby generating a corresponding output sinogram, and training the neural network by iteratively adjusting weighting coefficients of the neural network to minimize a value of a loss function, the loss function measuring a disagreement between the output sinogram and a target sinogram that corresponds to the given input sinogram used to generate the output sinogram, wherein the loss function includes a peak signal-to-noise ratio, a structural similarity index, and/or an $l_p$-norm of a difference between the respective target sinograms and filtered sinograms corresponding to the input sinograms, and the neural network is trained to generate output sinograms having enhanced resolution relative to the input sinograms by using the training dataset in which the second detector configuration used to acquire the target sinograms has a uniform pixel resolution corresponding to a pixel resolution of the first pixels.

19. The method according to claim 16, wherein the step of acquiring the neural network further includes that the neural network has been trained using the target data that is acquired using second detector configuration, which has a uniform pixel resolution corresponding to a pixel resolution of the first pixels, and the step of applying the projection data to the neural network further includes that the filtered projection output from the data neural network has a uniform pixel resolution of the first pixels.

20. A non-transitory computer-readable storage medium including executable instructions, which when executed by circuitry, cause the circuitry to perform the method according to claim 16.

* * * * *